US010871093B2

(12) United States Patent
Rüegg

(10) Patent No.: US 10,871,093 B2
(45) Date of Patent: Dec. 22, 2020

(54) MOTOR VEHICLE HAVING A CONTROL APPARATUS FOR AT LEAST ONE LOUDSPEAKER OF AN EXHAUST SYSTEM OF THE MOTOR VEHICLE

(71) Applicant: AUDI AG, Ingolstadt (DE)

(72) Inventor: Markus Rüegg, Friolzheim (DE)

(73) Assignee: AUDI AG, Ingolstadt (DE)

(*) Notice: Subject to any disclaimer, the term of this patent is extended or adjusted under 35 U.S.C. 154(b) by 357 days.

(21) Appl. No.: 16/073,603

(22) PCT Filed: Feb. 23, 2017

(86) PCT No.: PCT/EP2017/054178
§ 371 (c)(1),
(2) Date: Jul. 27, 2018

(87) PCT Pub. No.: WO2017/144592
PCT Pub. Date: Aug. 31, 2017

(65) Prior Publication Data
US 2019/0162090 A1   May 30, 2019

(30) Foreign Application Priority Data
Feb. 27, 2016  (DE) .......................... 10 2016 002 449

(51) Int. Cl.
*F01N 1/06*      (2006.01)
*G10K 9/13*      (2006.01)
(Continued)

(52) U.S. Cl.
CPC ............. *F01N 1/065* (2013.01); *B60Q 5/008* (2013.01); *G10K 11/178* (2013.01);
(Continued)

(58) Field of Classification Search
CPC .. F01N 1/06; F01N 1/065; B60Q 5/00; B60Q 5/008; B60Q 5/005; G10K 11/175;
(Continued)

(56) References Cited

U.S. PATENT DOCUMENTS 7,188,005 B2 * 3/2007 Toba .................... G10K 15/02
                                                  180/313
7,979,147 B1 * 7/2011 Dunn ................... G10K 15/02
                                                   700/94
(Continued)

FOREIGN PATENT DOCUMENTS

CN        1333419 A      1/2002
CN      101555818 A     10/2009
(Continued)

OTHER PUBLICATIONS

International Search Report for PCT/EP2017/054178 dated Apr. 12, 2017.
(Continued)

*Primary Examiner* — Edgardo San Martin
(74) *Attorney, Agent, or Firm* — Staas & Halsey LLP

(57) ABSTRACT

Combustion gas of an internal combustion engine passes through an exhaust system to an outlet opening. A detection device generates a state signal that describes an engine noise of the internal combustion engine. A control apparatus actuates at least one loudspeaker to produce a sound at the outlet opening based on the state signal to compensate for the engine noise or produce another engine noise, independently of the state signal based on predetermined audio data and thereby to use the at least one loudspeaker to audibly output an advisory signal described by the audio data.

10 Claims, 1 Drawing Sheet

(51) Int. Cl.
*B60Q 5/00* (2006.01)
*G10K 11/178* (2006.01)
*H04R 29/00* (2006.01)

(52) U.S. Cl.
CPC ........ *H04R 29/001* (2013.01); *B60Y 2306/11* (2013.01); *G10K 2210/12822* (2013.01); *H04R 2499/13* (2013.01)

(58) Field of Classification Search
CPC .......... G10K 11/178; G10K 9/12; G10K 9/13; G10K 9/22; G10K 15/02; G10K 15/10; G10K 15/12; G10K 2210/12822; B60R 16/02; B60Y 2306/11
See application file for complete search history.

(56) References Cited

U.S. PATENT DOCUMENTS

| | | | |
|---|---|---|---|
| 9,299,337 B2* | 3/2016 | Hera | G10K 15/02 |
| 2005/0232432 A1* | 10/2005 | Yasushi | B60Q 5/008 |
| | | | 381/17 |
| 2012/0109489 A1* | 5/2012 | Valeri | G10K 15/02 |
| | | | 701/102 |
| 2013/0230185 A1 | 9/2013 | Osawa et al. | |
| 2017/0206883 A1* | 7/2017 | Zintel | G10K 11/178 |

FOREIGN PATENT DOCUMENTS

| | | |
|---|---|---|
| CN | 104141521 A | 11/2014 |
| DE | 600 01 860 T2 | 11/2003 |
| DE | 102008037813 A1 | 5/2009 |
| DE | 102008064323 A1 | 6/2010 |
| DE | 102011051284 A1 | 7/2012 |
| DE | 102011116635 A1 | 4/2013 |
| DE | 102014001721 A1 | 10/2014 |
| DE | 202013006009 U1 | 11/2014 |
| DE | 102013221182 A1 | 4/2015 |
| DE | 102013112409 A1 | 5/2015 |
| DE | 102016002449.6 | 2/2016 |
| EP | 1 193 683 A2 | 4/2002 |
| GB | 2531878 A | 5/2016 |
| WO | 00/05489 | 2/2000 |
| WO | 2016/005580 A1 | 1/2016 |
| WO | 2016/026889 A1 | 2/2016 |
| WO | 2016/026890 A1 | 2/2016 |
| WO | PCT/EP2017/054178 | 2/2017 |

OTHER PUBLICATIONS

German Office Action for German Application No. 102016002449.6 dated Nov. 21, 2016.
English Translation by WIPO dated Aug. 30, 2018 of the International Preliminary Report on Patentability in corresponding International Patent Application No. PCT/EP2017/054178.
Office Action for Chinese Patent Application 201780006856.1 dated Mar. 4, 2019.

* cited by examiner

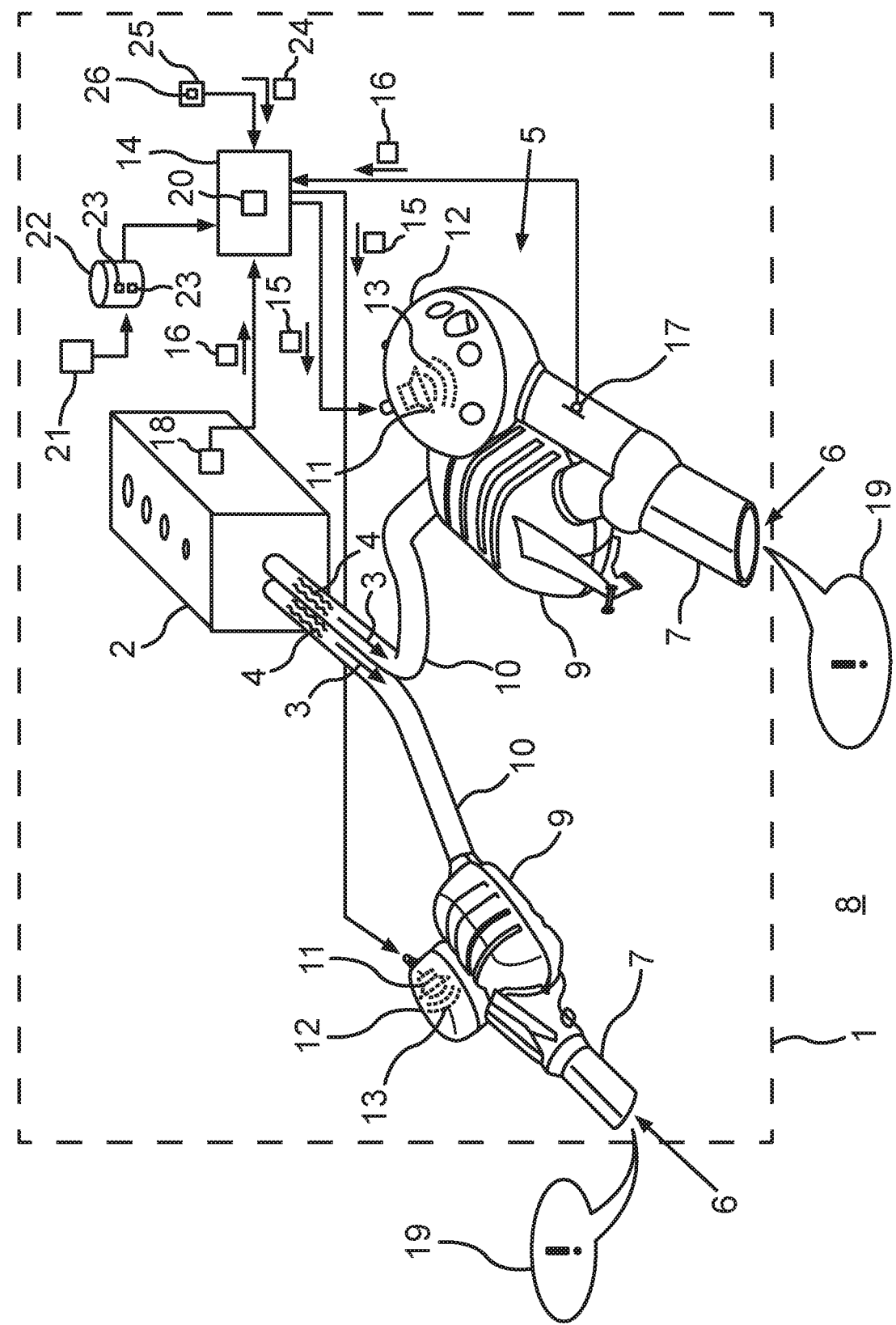

MOTOR VEHICLE HAVING A CONTROL APPARATUS FOR AT LEAST ONE LOUDSPEAKER OF AN EXHAUST SYSTEM OF THE MOTOR VEHICLE

CROSS REFERENCE TO RELATED APPLICATIONS

This application is the U.S. national stage of International Application No. PCT/EP2017/054178, filed Feb. 23, 2017 and claims the benefit thereof. The International Application claims the benefit of German Application No. 10 2016 002 449.6 filed on Feb. 27, 2016, both applications are incorporated by reference herein in their entirety.

BACKGROUND

Described below is a motor vehicle that has what is known as an active exhaust system. In other words, the exhaust system incorporates at least one loudspeaker that can emit a respective sound in a respective pipe of the exhaust system, in order, as a result, to compensate for an engine noise of an internal combustion engine of the motor vehicle and/or to at least partially replace it with a predetermined different engine noise, for example. Also described below is a corresponding method for controlling or operating the at least one loudspeaker.

An exhaust system having incorporated loudspeakers is known from DE 10 2013 112 409 A1. This has microphones provided in it for the purpose of picking up a current engine noise of an internal combustion engine of the motor vehicle. The microphone signals are used to generate an antiphase sound signal that is emitted into an end pipe of the exhaust system by the loudspeakers incorporated in the exhaust system, so that the engine noise and the antiphase sound compensate for one another. The engine noises are therefore less distinctly audible in surroundings of the motor vehicle.

DE 10 2013 221 182 A1 discloses the practice of emitting audible sound signals, for example a beep or click signal, from a motor vehicle into the vehicle surroundings, in order, as a result, to output a warning or advice to a person who is outside the motor vehicle. For this purpose, the motor vehicle requires dedicated loudspeakers, which make the motor vehicle more expensive to manufacture.

DE 10 2011 051 284 A1 describes a sound module for a motor vehicle that can be connected to a communication bus of the motor vehicle with a short signal path. However, this sound module is suitable only for use in the vehicle interior.

SUMMARY

The method described below delivers an advice signal from a motor vehicle into the vehicle surroundings.

A motor vehicle that has what is known as an active exhaust system has an internal combustion engine, which produces a combustion gas during operation, and an exhaust system for taking away the combustion gas from the internal combustion engine to at least one outlet opening. Such an outlet opening may be provided in a respective end pipe of the exhaust system, for example. A sensing device is set up to pick up a state signal that, during operation of the internal combustion engine, describes a current engine noise thereof and/or a current operating parameter characterizing operation. The sensing device can thus include a microphone, for example, that picks up the current engine noise. The sensing device may alternatively be set up to pick up a current speed of the internal combustion engine, for example, in order, as a result, to pick up the speed as an operating parameter. In addition, at least one loudspeaker is provided, which is set up to emit a sound into a respective pipe of the exhaust system toward the at least one outlet opening. The at least one loudspeaker thus produces the sound in the exhaust system, so that the sound comes out of the exhaust system to the outside with the at least one outlet opening. A control apparatus is set up to actuate the at least one loudspeaker to produce the sound on the basis of the state signal of the sensing device and, as a result, to use the sound produced to at least partially compensate for the engine noise and/or to at least partially replace it with a predetermined different engine noise. Thus, either the engine noise in the vehicle surroundings is reduced and/or a different engine noise, for example that of an internal combustion engine of a different engine type, is output or emitted.

To also output an advice signal to a person in the vehicle surroundings, the control apparatus may be set up to actuate the at least one loudspeaker additionally independently of the state signal, that is to say independently of the current engine noise and/or operating parameter of the internal combustion engine, on the basis of predetermined, stored audio data and, as a result, to use the at least one loudspeaker to audibly output an advice signal described by the audio data. The loudspeakers accordingly produce a sound that represents or carries the advice signal. The sound comes emitted by the exhaust system and the at least one outlet opening thereof into the vehicle surroundings, so that the advice signal becomes audible outside the motor vehicle. This advantageously requires no additional loudspeaker, since the at least one loudspeaker of the active exhaust system can be used to generate the audible advice signal.

The operation of the control apparatus of the motor vehicle results in a method for operating the control apparatus for the at least one loudspeaker of the exhaust system has provision for the control apparatus to actuate the at least one loudspeaker to produce a sound on the basis of the described state signal and, as a result, to use the sound produced by the at least one loudspeaker to at least partially compensate for the engine noise described by the state signal and/or to at least partially replace it with a predetermined different engine noise. Additionally, the control apparatus may actuate the at least one loudspeaker at the same time and/or at a different time independently of the state signal, on the basis of predetermined stored audio data, and, as a result, to use the at least one loudspeaker to output an advice signal described by the audio data.

The optional developments described below result in additional advantages.

Since the advice signal is generated independently of the state signal, it is therefore also independent of operation of the internal combustion engine. Accordingly, a development provides for the control apparatus to be set up to output the advice signal with the internal combustion engine switched off or turned off. The internal combustion engine produces no engine noise. The ignition of the motor vehicle may be switched off. This results in the advantage that such an advice signal can be generated that a user of the motor vehicle can receive while he is operating the motor vehicle from outside same, for example locking the motor vehicle.

A development provides for the advice signal to be generated specifically on the basis of at least one predetermined event. In this regard, a detection device may be provided to detect at least one predetermined output situation and in each case to signal this output situation by a trigger signal that is independent of the state signal. The control apparatus is set up to take the trigger signal as a basis for outputting the advice signal. An output situation of this kind or an output event can be detected in each case by a detection device, which may be configured according to the output situation to be detected. By way of example, as one possible detection device, an alarm system can generate the trigger signal in the event of burglary attempt. The development results in the advantage that the advice signal is generated as audible feedback pertaining to the detected output situation and, as a result, a user of the motor vehicle or else a person in the vehicle surroundings can be informed or warned.

A development in this regard provides for the detection device to be set up to detect as output situation a parking phase of the motor vehicle in which the motor vehicle is parked or switched off and at least the driver of the motor vehicle has got out of the motor vehicle. The advice signal can therefore e.g. signal to the driver who has got out that the motor vehicle is ready or set for the parking phase. By way of example, it may thus be signaled that an electrical load is no longer being operated unnecessarily, such as the infotainment system (information/entertainment system) and/or the vehicle luminaire, for example, and/or that the alarm system has been activated. As a result, it is also possible to signal that there is still a need for action, for example because a window of the motor vehicle and/or a sunroof are open. Appropriate detection devices for detecting the states described are providable as known in the related art.

A development provides for the detection device to be set up to detect as output situation a change of state of a locking system for vehicle doors of the motor vehicle. In other words, the advice signal is generated when the motor vehicle is locked and/or unlocked. This results in the advantage that the successful operation of the locking system is signaled to a user of the motor vehicle. Also, a motor vehicle can use the advice signal to indicate where it is located when a radio key is used.

A development provides for the detection device to be set up so as, after detecting an output situation, to generate the associated trigger signal with a predetermined time delay. The time delay may be preset or can be produced by a random number generator, for example. Providing a time delay results in the advantage that a user of the motor vehicle is given time to get into position to be able to use the advice signal. By way of example, in this way, after the motor vehicle is unlocked by a radio key, it is first possible to await an approach by a user without complex detection of a position of the user being necessary. It is simply assumed that the user is not standing next to the motor vehicle until after the time delay.

A development provides for the detection device to be set up to detect as output situation a predetermined operating action by a user using an operator control device for the motor vehicle. By way of example, it is possible to detect that a user operates a locking key on a radio key in accordance with a predetermined control pattern, for example presses twice in succession. This results in the advantage that the advice signal can be triggered or controlled specifically by the user. It is thus possible for the user to use the operating action, for example, to have the output of the advice signal regarding the open window and/or electrical loads still operating output and, as a result, to check whether the motor vehicle is set for parking or ready for parking.

An embodiment provides for the detection device to be set up to detect as output situation a reverse gear selected with the internal combustion engine running. This results in the advantage that the at least one loudspeaker is used to output a warning about possible reversing of the motor vehicle into the vehicle surroundings as the advice signal. The advice signal may then be, by way of example, rattling or rustling or a sound in order to direct the attention of a person in the vehicle surroundings to the motor vehicle.

A development provides for the control apparatus to be set up to generate the advice signal only if at least one predetermined driving mode from multiple activable driving modes of the motor vehicle is activated in the motor vehicle. A driving mode is distinguished in that it stipulates a predetermined mode of operation of the internal combustion engine and/or of a chassis of the motor vehicle. Every driving mode sets a different mode of operation in this case. It is therefore possible for the output of the advice signal to be limited or restricted to a sports driving mode, for example.

Naturally, according to one development, there is also provision for a user of the motor vehicle to be able to use an operating or operator control device to activate and selectively deactivate the output of the advice signal.

A development provides for the control apparatus to be set up to output a beating, in particular an imitated heartbeat, as the advice signal. A beating as the advice signal has the advantage that an advice signal of this kind is still perceptible in the vehicle surroundings even if the at least one pipe in which the sound is emitted by the at least one loudspeaker has an acoustic transfer characteristic that has a frequency-dependent magnitude response attenuating frequencies of the sound in different ways. A beating is distinguished not primarily by the spectrum of its frequencies but rather by its modulation over time. This modulation is not impaired by the extremely linear response of a pipe, however.

Naturally, there may also be provision for a melody and/or a noise to be output as an advice signal. This may be adapted to take into consideration the acoustic transfer characteristic of the exhaust system, so that a desired target noise is audible or perceptible or measurable in the vehicle surroundings after the emergence of the sound from the at least one outlet opening.

A development provides for a configuration device to be set up to set the audio data on the basis of a user input and/or to select them from multiple predetermined audio data records. In other words, a user can set what advice signal is supposed to be output. By way of example, an MP3 file may thus be prescribed as a respective audio data record. The user can then use the configuration device, which may be implemented by the infotainment system, for example, to select those audio data that are supposed to be reproduced by the control apparatus by the at least one loudspeaker.

The motor vehicle may be an automotive vehicle, in particular as an automobile or truck.

The developments of the method include features as have already been described in connection with the developments of the motor vehicle. For this reason, the applicable developments of the method are not described again here.

The text below describes an exemplary embodiment. In this regard, the single FIGURE (FIGURE) shows a schematic depiction of an embodiment of the motor vehicle.

In the exemplary embodiment, the described components are each individual features that are to be considered independently of one another and can also be regarded individually or in a combination other than what is shown. In addition, the described embodiment can also have further features that have already been described added to it.

BRIEF DESCRIPTION OF THE DRAWINGS

These and other aspects and advantages will become more apparent and more readily appreciated from the following description of the exemplary embodiments, taken in conjunction with the accompanying drawings of which:

The single FIGURE is a combined schematic block diagram and perspective view.

DETAILED DESCRIPTION OF THE PREFERRED EMBODIMENT

Reference will now be made in detail to the preferred embodiments, examples of which are illustrated in the accompanying drawings, wherein like reference numerals refer to like elements throughout.

The FIGURE shows a motor vehicle 1, which may be an automotive vehicle, in particular an automobile, for example. The motor vehicle 1 has an internal combustion engine 2, which may be a diesel engine or a gasoline engine, for example. During operation or in the switched-on state, the internal combustion engine 2 produces a combustion gas 3 and engine noises 4, which are guided or routed through an exhaust system 5 of the motor vehicle 1 to at least one outlet opening 6 of the exhaust system 5 in a manner known per se. The at least one outlet opening 6 may be formed by a respective end pipe 7 of the exhaust system 5, for example. The outlet opening 6 allows the combustion gas 3 and the engine noise 4 to escape to vehicle surroundings 8. Of the exhaust system 5, the muffler 9 and the pipe 10 coupling or connecting the muffler 9 to the internal combustion engine 2 are depicted in addition for the purpose of illustration. The internal combustion engine 2 is therefore coupled or connected to the respective outlet opening 6, for example in an end pipe 7, via at least one pipe 10 and at least one muffler 9.

In the motor vehicle 1, the exhaust system 5 additionally has at least one loudspeaker 11, which may be arranged in a loudspeaker container 12 in each case, for example. Each loudspeaker 11 can produce a sound 13 that is emitted by the loudspeaker 11 in the exhaust system 5, for example to the end pipe 7 toward the outlet opening 6, or reaches that point. In this case, the loudspeaker container 12 can reflect or guide or focus the sound 13 toward the outlet opening 6.

The at least one loudspeaker 11 can be controlled or operated by a control apparatus 14. The control apparatus 14 may to that end be implemented on the basis of a controller of the motor vehicle 1, for example. To control the at least one loudspeaker 11, the control apparatus 14 generates a respective loudspeaker signal 15. The loudspeaker signal 15 is generated by the control apparatus 14 in this case on the basis of at least one state signal 16 that describes the engine noise 4. By way of example, a state signal 16 can be generated by a microphone 17 that picks up the engine noise 4 in the exhaust system 5. A speed sensing device 18 can ascertain and signal a current speed of the internal combustion engine 2, for example, as a state signal 16. The control apparatus 14 can take the at least one state signal 16 as a basis for generating the loudspeaker signal 15 in a manner known per se such that the engine noise 4 is reduced at the at least one outlet opening 6 by destructive interference. Additionally or alternatively, there may be provision for the loudspeaker signal 15 to be used to produce an engine noise differing from the engine noise 4 as sound 13, so that an engine noise of a different engine type can be heard in the vehicle surroundings 8.

In the motor vehicle 1, the at least one loudspeaker 11 is additionally used or operated to generate or emit an audible advice signal 19 in the vehicle surroundings 8. This advice signal 19 is independent of the operation of the internal combustion engine 2 in terms of sound and output time. The advice signal 19 is emitted by the at least one loudspeaker 11. The applicable loudspeaker signal 15 can be generated on the basis of audio data 20 that describe a melody and/or an announcement and/or a beating and/or a noise as the advice signal 19, for example. There may be provision for a user to use a configuration device 21 to select from a data memory 22 an audio data record 23 stored therein and to stipulate the selected audio data record as the audio data 20 in the control apparatus 14. The control apparatus 14 can produce the audio data 20 as the audible advice signal 19 by the at least one loudspeaker 11 in the vehicle surroundings 8 whenever it receives a predetermined trigger signal 24. The trigger signal 24 can be generated by a detection device 25, which generates the trigger signal 24 whenever it detects a predetermined output situation 26. By way of example, the output situation 26 may be a motor vehicle 1 having been switched off and/or locked.

Thus, if the motor vehicle 1 has an active exhaust system 5 fitted in order to simulate an engine sound of a larger-volume internal combustion engine than the internal combustion engine 2, the control apparatus 14 can also be used, using the at least one loudspeaker 11 of the active exhaust system 5, to produce an audible trademark or advice signal 19 in a predetermined output situation 26 via the at least one loudspeaker 11. Therefore, a trademark jingle or a characteristic audible advice signal 19, for example, is audible outside the motor vehicle 1 in the adjacent vehicle surroundings 8. It is thus possible for a heartbeat to be output as an advice signal 19, for example, in order, as a result, to provide a goodbye signal or a welcome signal for a user of the motor vehicle 1 in the vehicle surroundings 8, for example.

Overall, the example shows how to reproduce trademark-based jingles using an active exhaust system (AGA).

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

The invention claimed is:

1. A motor vehicle, comprising:
    doors;
    a locking system for the doors;
    an internal combustion engine producing a combustion gas during operation;
    an exhaust system having at least one pipe taking away the combustion gas, during operation of the internal combustion engine, to at least one outlet opening of the exhaust system;
    a sensing device generating a state signal, during operation of the internal combustion engine, that describes at least one of a current engine noise and a current operating parameter characterizing operation;
    a detection device configured to detect a predetermined output situation, including at least one change of state of the locking system, and to generate a trigger signal in response to the predetermined output situation;
    at least one loudspeaker configured to emit a sound into a respective pipe of the exhaust system toward the at least one outlet opening; and
    a control apparatus configured to actuate the at least one loudspeaker to produce the sound based on the state signal to at least partially compensate for the current engine noise and/or to at least partially replace the current engine noise with a predetermined other engine noise, and, independently of the state signal, based on predetermined stored audio data, to audibly output an advice signal described by the audio data in response to the trigger signal that is independent of the state signal and generated in the predetermined output situation with a predetermined time delay.

2. The motor vehicle as claimed in claim 1, wherein the control apparatus is configured to output the advice signal with the internal combustion engine switched off.

3. The motor vehicle as claimed in claim 2, wherein the detection device is configured to detect as the predetermined output situation a parking phase in which the motor vehicle is parked and a driver has exited the motor vehicle.

4. The motor vehicle as claimed in claim 1, wherein the detection device is configured to detect as the predetermined output situation a parking phase in which the motor vehicle is parked and a driver has exited the motor vehicle.

5. The motor vehicle as claimed in claim 1,
further comprising an operator control device, and
wherein the detection device is configured to detect as the predetermined output situation a predetermined operating action by a user of the operator control device for the motor vehicle.

6. The motor vehicle as claimed in claim 5,
further comprising a transmission having a reverse gear and at least one forward gear, and
wherein the detection device is configured to detect as the predetermined output situation the reverse gear selected with the internal combustion engine running.

7. The motor vehicle as claimed in claim 5,
further comprising a chassis, and
wherein the control apparatus is configured to generate the advice signal only when at least one predetermined driving mode from multiple activable driving modes, each of which stipulates a different mode of operation of at least one of the internal combustion engine and the chassis of the motor vehicle, is activated in the motor vehicle.

8. The motor vehicle as claimed in claim 1,
further comprising a chassis, and
wherein the control apparatus is configured to generate the advice signal only when at least one predetermined driving mode from multiple activable driving modes, each of which stipulates a different mode of operation of at least one of the internal combustion engine and the chassis of the motor vehicle, is activated in the motor vehicle.

9. The motor vehicle as claimed in claim 1, wherein the control apparatus is configured to output an imitated heartbeat, as the advice signal.

10. The motor vehicle as claimed in claim 1, further comprising a configuration device configured to set the audio data based on at least one of a user input and from among multiple predetermined audio data records.

* * * * *